Figure 1:
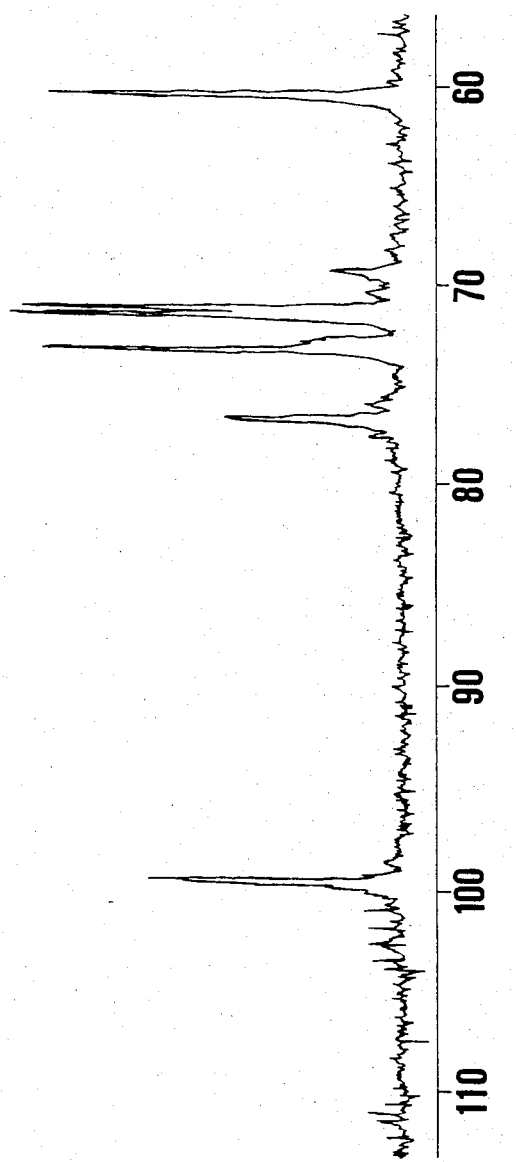

United States Patent [19]

Vellini

[11] Patent Number: 4,507,286

[45] Date of Patent: Mar. 26, 1985

[54] POLYSACCHARIDE HAVING ANTIINFLAMMATORY AND PLATELET ANTIAGGREGATION ACTIVITY

[75] Inventor: Massimiliano Vellini, Saronno, Italy

[73] Assignee: Rorer Italiana, S.P.A., San Fruttuoso di Monza, Italy

[21] Appl. No.: 476,230

[22] Filed: Mar. 17, 1983

[30] Foreign Application Priority Data

Mar. 22, 1982 [IT] Italy ............................... 20313 A/82
Feb. 18, 1983 [IT] Italy ............................... 47744 A/83

[51] Int. Cl.$^3$ ..................... A61K 31/715; C08B 37/00
[52] U.S. Cl. .................................... 514/23; 424/118; 536/1.1; 536/128
[58] Field of Search ................. 424/118, 180; 536/1.1, 536/128

[56] References Cited

U.S. PATENT DOCUMENTS 3,780,017 12/1973 Spalt et al. ........................... 536/128
4,119,435 10/1978 Nakao et al. ......................... 536/128

FOREIGN PATENT DOCUMENTS 3042491 7/1982 Fed. Rep. of Germany ...... 536/128

OTHER PUBLICATIONS

Hiramatsu, "Chem. Abst.", vol. 72, 1970, p. 11264(h).
Murachi, "Chem. Abst.", vol. 75, 1971, p. 84371(f).
Golding, "Chem. Abst.", vol. 77, 1972, p. 45,752(c).
Taussig, "Chem. Abst.", vol. 92, 1980, p. 140245(h).
Tanimoto et al., "Chem. Abst.", vol. 93, 1980, p. 31829(b).
Izaka et al., Gastrointestinal Absorption and Antiinflammatory Effect of Bromelain, 1972, pp. 519–534.
Netti Il Farmaco Fd. Pr. Vol. 27, pp. 453–465.

*Primary Examiner*—Johnnie R. Brown
*Attorney, Agent, or Firm*—Bucknam and Archer

[57] ABSTRACT

The extraction is described of a substance endowed with antiinflammatory and platelet antiaggregation activity, starting from the juice of plants of the species Ananas, Bromelia, Karatas, etc. of the family Bromeliaceae, or extractable from their derivatives such as bromelain. The extraction may be made by means of thermo-coagulation or precipitation by trichloracetic acid, starting both from raw juices obtained from their roots or from the fruits, and from previously isolated bromelain.

8 Claims, 3 Drawing Figures

POLYSACCHARIDE HAVING ANTIINFLAMMATORY AND PLATELET ANTIAGGREGATION ACTIVITY

The present invention relates to the isolation of a new active principle endowed with a high antiinflammatory and platelet antiaggregation activity starting from the raw juices of plants of the family Bromeliaceae or by adequately treating an extract named bromelain, because it is mainly constituted by bromelain, a group of proteolytic enzymes contained in fruits or stems of such plants. The term bromelain will be used in the present application hereinbelow to designate the extract containing said enzymes. Such an extract has been used for a long time in the pharmaceutical and dietary field, because of its antiinflammatory properties, and it is obtained by treatment with acetone or methanol, or again by saturation with ammonium sulfate of the juice obtained from the roots or fruits of the plants of the species Ananas.

The antiinflammatory properties of the bromelain are however exerted in a reduced manner, probably as a result of the prevalent enzymatic and proteolytic activity.

With this background, the applicant has conducted research studies meant to enhance the interesting antiinflammatory activity and possibly to isolate the active substance responsible for this activity.

The object of the present invention is therefore that of providing a process capable of isolating and identifying this active substance. The research has resulted in the finding of an active substance, non-proteinaceous in nature and deprived of enzymatic activity, obtained from the juice of plants of the species Ananas and secondarily Bromelia and Karatas. This active substance displays a high platelet antiaggregation and antiinflammatory activity much more marked than that of bromelain or its acetone methanolic precipitate or obtained by saturation with ammonium sulfate of the juice itself.

The new active substance is prepared by means of a fractional precipitation carried out with a water soluble alcohol (such as ethanol, methanol, 2-propanol) on the clear liquid obtained by deproteination of the above mentioned juice or bromelain, preferably in the presence of an antioxidant agent, such as sodium metabisulphite.

The procedure already briefly mentioned and the substance so obtained will be now described in detail on the basis of a few examples reported for the sake of illustration and which are therefore not restrictive.

EXAMPLE 1

Procedure for obtaining the substance starting from the juice by means of thermocoagulation A solution of sodium hydroxide is added to the aqueous juice till a pH 6 to 12 is reached, and the solution is heated under shaking till 95° C. This temperature must be maintained for 5 minutes and then the solution is left to cool to the temperature of 10°–15° C. The pH is later brought to 5.5 by means of dilute hydrochloric acid, which causes a massive precipitation of proteins. The mass so separated is removed by means of filtration under pressure and the clear liquid resulting from the operation is brought to pH 4.0–4.5 by means of dilute hydrochloric acid.

To the total volume of liquid so obtained, a quantity of 95° ethyl alcohol equal to 0.3–0.6 times of the volume is added. A new precipitate is formed, which is separated by filtration. To the clear liquid resulting after removal of the precipitate, about 1–2 volumes of ethyl alcohol is added, with formation of a new precipitate which is collected by centrifugation, washed in 80% ethyl alcohol and filtered. The residue of the filtration, composed of the active substance, is later washed with ethyl alcohol, acetone and ethyl ether and finally is vacuum-dried. The yield is equal to about 0.010% of the weight of the roots and to about 0.002% of the weight of the fruits.

EXAMPLE 2

Procedure for obtaining the substance starting from the juice by means of precipitation with trichloroacetic acid Trichloroacetic acid up to a 5% concentration and sodium metabisulphite (1%) are added to the juice: the solution is then shaken for about 10 minutes till formation of a precipitate which is separated by filtration. The pH of the clear liquid is brought to about 4.0–4.5 by adding a dilute solution of sodium hydroxide.

The operation is completed as described under Example 1.

The yield in this case is equal to 0.005% of the weight of the roots and to about 0.001% of the weight of the fruits.

EXAMPLE 3

Procedure for extracting the substance starting from "bromelain" by means of thermocoagulation Bromelain is suspended in 10 volumes of distilled water and the procedure is continued carrying out all the phases described under Example 1. The yield of active substance is equal to about 2.0% in weight as compared with the initial quantity of bromelain.

EXAMPLE 4

Procedure for extraction starting from bromelain by means of precipitation with trichloroacetic acid Bromelain is suspended in 10 volumes of distilled water, in the presence of sodium metabisulphite (1%), and then all the operations under Example 2 are carried out, and completed with the further steps according to Example 1.

The yield in this case is about 0.5% as compared with the initial quantity of bromelain.

The product obtained according to the Examples so far described has the appearance of a white odorless powder, m.p. above 280° C., moderately soluble in water. Solubility is maintained also in hydroalcoholic solution up to a low concentration of ethyl alcohol concentration, till it stops at an alcohol concentration of 50%. Furthermore the substance is generally insoluble in organic solvents.

If treated by means of alpha-naphthol in the presence of sulphuric acid, the product obtained gives the characteristic reaction of carbohydrates. For identification purposes, an electrophoresis on cellulose acetate at pH 9.5 at 200 V for one hour was performed.

The analysis was carried out by putting about 10 microliter of an aqueous solution of the product at 2% and developing with the Schiff reagent. A band appears at about 1.5 cm from the deposition point.

Using the HPLC technique, the compound on C18 Bondapack column 300 mm×4 (15.000 plates/m) at a flow-rate of 1 ml/min. with eluent water, has a retention time of 8.2 minutes (detector: refractive index).

$C^{13}$-NMR Spectrum

The spectrum, recorded in $D_2O$, has signals at 99.6 ($C_1$ in the saccharidic unit), 76.8 ($C_4$), 73.4 ($C_3$), 71.5 and 71.1 ($C_2$ and $C_5$), 60.5 ppm ($CH_2OH$).

Figure 2:
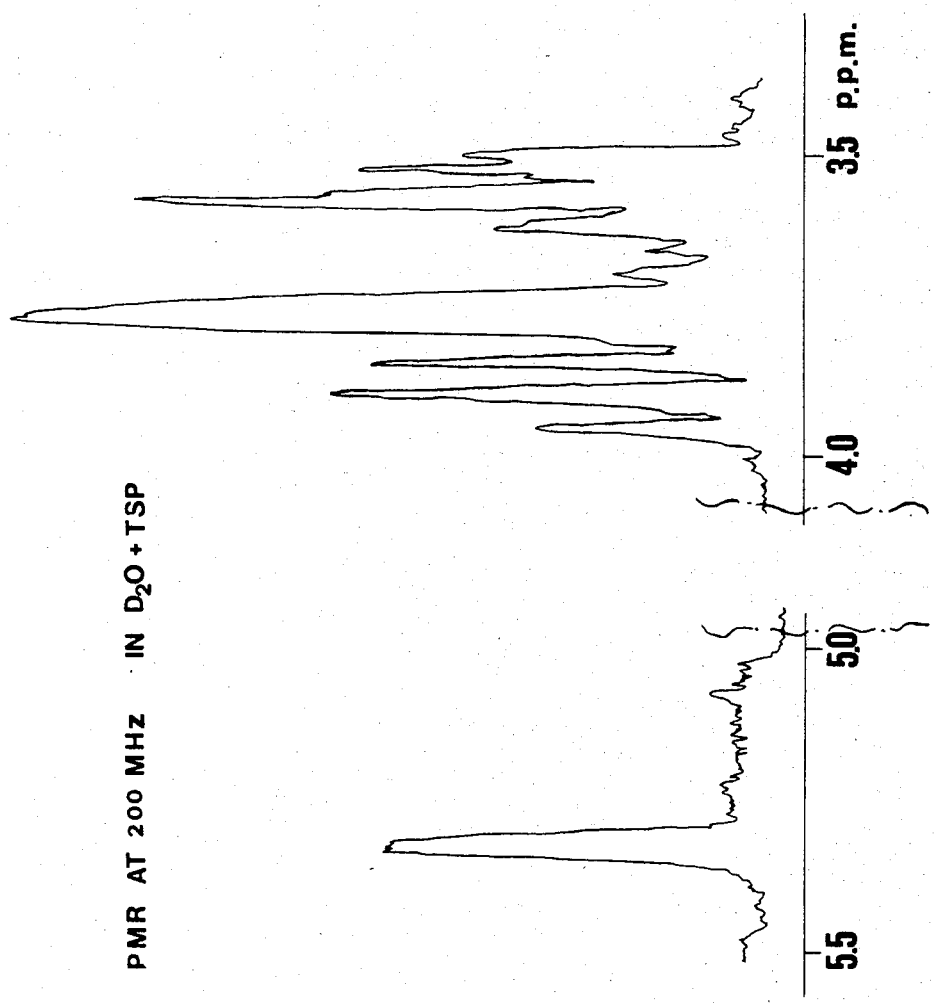

$H^1$-NMR Spectrum:

recorded in $D_2O$+TSP at 200 MHZ, it shows signals typical for a polysaccharidic compound. The signal of the hydrogen in position 1 of the saccharidic unit is the one at lower fields (FIG. 2).

IR Spectrum: recorded in KBr, it shows broad bands in the 3600–3000 and 1200–1000 cm$^{-1}$ regions.

[$a_D$]: (C=0.6 in $H_2O$): it stabilizes after a few hours in solution at values comprised from +120° to +140°.

Elemental analysis:

C=45.0%; H=6.0%; O=48.0%; Na=0–2.0%; traces of S, Ca, N.

Thermogravimetric analysis:

The decomposition of the product starts at 230°–250° C., taking place thereafter vigorously above 290° C.

Titration of reducing sugars

The reducing sugars have been titrated by measuring spectrophotometrically the colour disappearance of a solution obtained by dissolving 1.16 g of potassium ferricyanide, 10 g of sodium phosphate dihydrate and 2.2 g of sodium hydroxide in 1 liter of water.

The reading was performed at 420 nm on a sample prepared by adding to a water solution (6 ml) of the compound to be titrated, 3 ml of ferricyanide solution. The blank was prepared from 6 ml of water and 3 ml of the ferricyanide solution and the calibration curve has been obtained with a glucose solution (20 mg/l). One reducing unit turned out to be present every 50 saccharidic units. The compound of the invention will be referred hereinafter by the compound obtained according to the processes described in the examples and endowed with the chemico-physical characteristics up to now reported.

The pharmacological characteristics found in the product obtained by means of the above mentioned procedures and having the reported chemico-physical characteristics have been assessed on the basis of investigations made on laboratory animals.

Acute Toxicity

Male Sprague-Dawley rats, weighing 120–150 g, fasted for 12 hours, were treated both by the oral route (gastric tube) and by intraperitoneal route with the compound of the invention (1 mg/kg) dissolved in deionized water in a volume of 0.01 ml/g body weight. At this dose, neither death in the rats (10 p.o. and 10 i.p.) at the 15$^{th}$ day after treatment nor changes of the behaviour and of food and water intake, indexes of toxic effects, have been noticed. The dose of 1 mg/kg is about 1 billion times higher than the pharmacologically active dose.

Subacute toxicity

The study of the toxicity after repeated administrations has been performed on Sprague-Dawley rats of both sexes, divided in groups of 10 animals each, treated by the oral route for 12 weeks at the doses of 1 mg/kg, 1 µg/kg and 1 ng/kg. At the end of the treatment no toxic effect, also in the highest dose level group, has been noticed.

Mutagenesis and DNA-lesive activity

The product proved to be devoid of mutagenic activity: in fact, the Ames test turned out negative.

The possible "in vivo" DNA-damaging activity, which can be related with the potential carcinogenic activity, has also been studied. It has been used the alkaline elution method according to Kohn et al. (Biochemistry, 15, 4629, 1979) and subsequent modifications (Cancer Res. 38, 1589, 1978; Int. J. Cancer 22, 174, 1978; Gann 71, 251, 1980).

From the results obtained on the DNA extracted by the livers and kidneys of rats treated with 1 mg/kg of the compound of the invention by intragastric route and sacrificed after 4 hours, DNA damaging effects, detectable by the alkaline elution technique, were not found.

Antiinflammatory activity (a) Ascite by formalin

It has been used the method described by Teotino et al. (J. Med. Chem. 6, 248, 1963).

Male, Sprague-Dawley rats, divided in 2 groups, have been treated at the hours 0 and +1 with 0.3125 and 1.25 picograms/kg by intragastric route of the compound of the invention, in a volume of deionized water of 0.01 ml/g body weight, a control group being treated at the same times with an equal volume of deionized water.

At the hour +1 (one hour after the first treatment), all the rats were injected i.p. with 1 ml of a 1.5% (w/v) formalin aqueous solution.

After 5 hours the animals were sacrificed, the ascitic liquid was removed and weighed.

In the animals in which the liquid was so scarce as to be not measurable, it has been assigned the arbitrary value of 100 mg/kg. From the results reported in the following Table it is evident that the compound of the invention, in the used experimental conditions, is endowed with a remarkable antiinflammatory activity even at very low doses, with an $ED_{50}$ lower than 0.3125 picograms/kg (pg/kg).

TABLE 1

| Groups | Dose (pg/kg) | % Inhibition of ascitic liquid, expressed as mg/kg, versus controls | P* |
|---|---|---|---|
| Controls | — | — | |
| 1 | 0.3125 | 60.54 | <0.01 |
| 2 | 1.25 | 58.53 | <0.01 |

*Significance according to the Tukey test.

(b) Granulomatous tissue by croton-oil

It has been used the method described by Fisher (J. Pharmacol. Exp. Ther. 132, 232, 1961), modified by us.

Male, Sprague-Dawley rats, weighing 150–200 g, divided in 3 groups per dose and a control group, have been treated with the compound of the invention at the doses of 25-100-400 picograms/kg/die by intragastric route in a volume of deionized water of 0.01 ml/kg for 4 consecutive days. The control group was treated with an equal volume of deionized water. Contemporaneously, the granulomatous pocket was prepared by injecting on the first day (one hour after first treatment) 0.5 ml of a 1% (w/v) sterile solution of croton oil in seed oil into an air pocket obtained by injecting 25 ml of sterile air into the back's subcutaneous tissue.

After air aspiration (second day), on the 4$^{th}$ day (one hour after the last treatment) the granulomatous tissue has been removed and weighed, with an accuracy of ∓50 mg (scoring 100 mg/kg those animals in which the granulomatous tissue was virtually absent, considering not correct its total absence).

From the results reported in the Table 2 a statistically significant reduction (Wilcoxon test; bidirectional two sample test) of the exudate neoformation has been observed, with an $ED_{50}$ lower than 25 picograms/kg (pg/kg).

TABLE 2

| Groups | Dose pg/kg | % Inhibition granu lomatous tissue, expressed in mg/kg, versus controls | P* |
|---|---|---|---|
| Controls | — | — | |
| 1 | 25 | 80.3 | 0.05 |
| 2 | 100 | 86.6 | <0.05 |
| 3 | 400 | 84.2 | <0.05 |

*Significance: Wilcoxon two sample test (bidirectional)

(Evaluation of Drug Activities: Pharmacometries", D. R. Laurence and A. L. Bacharach (eds.), Vol. 1, pp. 80–82, Academic Press, N.Y., 1964).

Platelet antiaggregant activity

The product was orally administered at concentrations of 100, 50, 20 and 10 picograms/kg in physiologic solution to groups of Sprague-Dawley rats, mean weight ab. 300 g, kept fasting for 24 hours. Blood samples were taken intracardially, and on the adequately diluted serum platelet aggregation tests with ADP were performed in comparison with untreated rats.

On the basis of the results obtained an effective dose 50%, lower or equal to 10 picograms/kg was established.

As it may easily be seen from the data reported, the product of the present invention displays an extremely high activity both as antiinflammatory agent and platelet antiaggregation agent, and the useful therapeutic margin appears to be extremely wide, so as to expect for it a safe therapeutic use in humans, particularly in pharmaceutical forms at doses ranging from 5 to 5000 pg for a unit dose, even if higher and lower dosages can be used.

Since both the inflammatory condition and the platelet aggregation are to be ascribed to the effects of stimulation/inhibition of prostaglandin synthesis, the product of the present invention may be adopted in all the cases in which it is advisable to interfere with the said mechanism of stimulation/inhibition of prostaglandins, and particularly in the cases for which the elective therapeutic modality is one by means of an platelet antiaggregation drug, such as prevention and treatment of heart infarction, arteriosclerosis and related diseases, or by means of an antiinflammatory agent, in conditions such as arthritis, arthrosis and inflammatory diseases in general.

The present invention refers also to all the industrially applicable aspects connected with the use of the compound of the invention as antiinflammatory and platelet antiaggregation agent. An essential aspect of the invention is therefore provided by pharmaceutical compositions containing predetermined and therapeutically effective amounts of the compound of the invention, suitable for the administration by the oral, rectal, parenteral, topical or inhalatory routes such as drops, oral solutions, syrups, capsules, tablets, creams, ointments, suppositories, vials for injection, aerosol, possible forms with a controlled release of active principle, for instance obtained by microencapsulation etc.

Even though the present invention has been described and illustrated on the basis of a few specific examples for its realization, it is obvious that variations and/or amendments which might be made by experts, are also within the scope of the invention. Therefore, other alkalinizing, acidifying and precipitating agents might be adopted, such as potassium hydroxide, acetic acid, methanol, etc.

Figure 3:
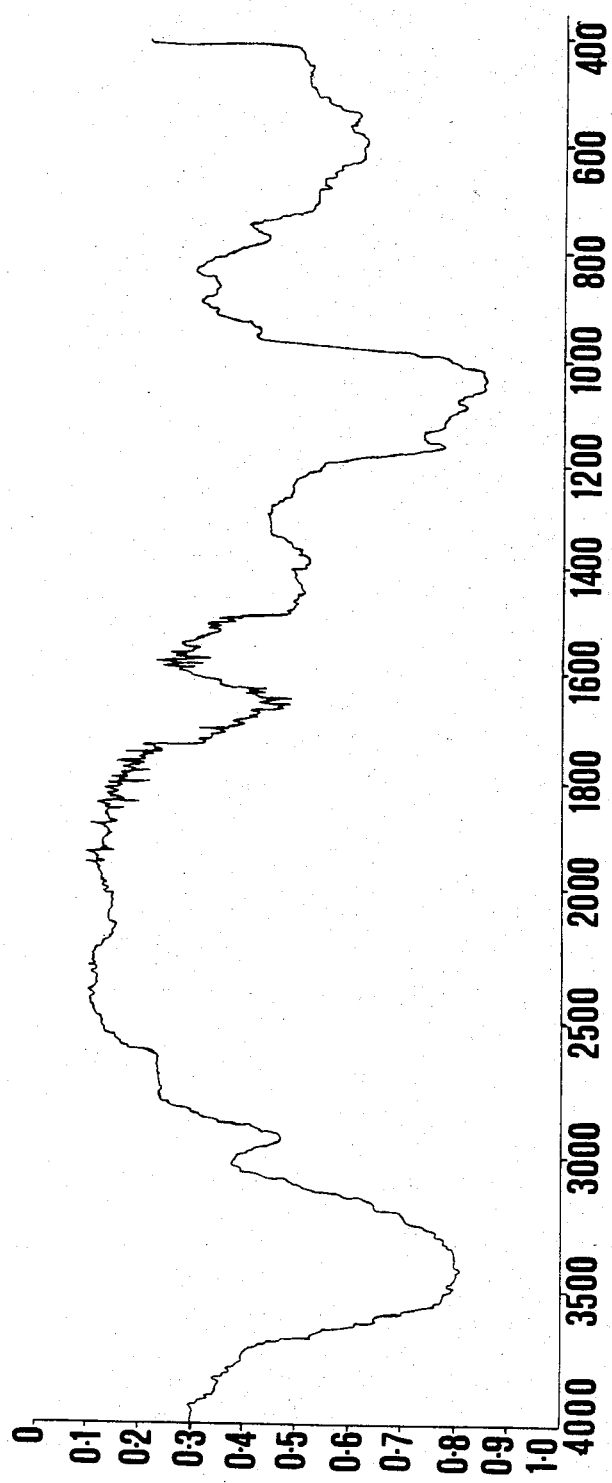

I claim:

1. The product with antiinflammatory and platelet antiaggregation activity obtained from bromelain or the juice of plants of the family Bromeliaceae, having an activity in the amount of 5–5000 picograms per unit dose, having the following characteristics:

substantially polysaccharidic nature and substantially protein-free;

degradation point higher than 280° C.;

and $\alpha_D$ value stabilized after a few hours in solution ranging from $+120°$ and $+140°$;

a retention time of 8.2 min. in HPLC on C18 Bondapack column 300 mm×4 (15,000 plates/m) at a flow-rate of 1 ml/min. of water as eluent;

a $C^{13}$ NMR spectrum showing signals at 99.6, 76.8, 73.4, 71.5, 71.1, and 60.5 ppm;

a $H^1$-NMR spectrum according to FIG. 2;

an IR spectrum according to FIG. 3, having broad bands in the region 3600–3000 and 1200–1000 $cm^{-1}$;

an elementary composition of about C=45%; H=6%; O=48%, Na from 0 to 2%.

2. The process for the extraction of a product with antiinflammatory activity and platelet antiaggregation activity, from the juice of plants of the family Bromeliaceae or from bromelain, said product having an activity in the amount of 5–5000 picograms per unit dose, having the following characteristics:

substantially polysaccharidic nature and substantially free of proteins;

degradation point higher than 280° C.;

an $\alpha_D$ value stabilized after a few hours in solution ranging from $+120°$ and $+140°$;

a retention time of 8.2 min. in HPLC on C18 Bondapack column 300 mm×4 (15,000 plates/m) at a flow-rate of 1 ml/min. of water as eluent;

a $C^{13}$ NMR spectrum showing signals at 99.6, 76.8, 73.4, 71.5, 71.1, and 60.5 ppm;

a $H^1$-NMR spectrum;

an IR spectrum having broad bands in the region 3600–3000 and 1200–1000 $cm^{-1}$;

an elementary composition of about C=45%; H=6%, O=48%; Na from 0 to 2%, which consists of thermocoagulating said juice or bromelain to precipitate the proteins, separating the precipitate from the filtrate, adjusting the pH of the filtrate to 4.0–4.5, adding ethyl alcohol in a ratio of 0.3–0.6:1 volumes, separating the precipitate, adding to the filtrate ethyl alcohol in a ratio of 1–2:1 volumes, separating the precipitate and recovering said product from the precipitate.

3. The process for the extraction of a product with antiinflammatory activity and platelet antiaggregation activity, from the juice of plants of the family Bromeliaceae or from bromelain, said product having an activity in the amount of 5–5000 picograms per unit dose, having the following characteristics:

substantially polysaccharidic nature and substantially free of proteins;

degradation point higher than 280° C.;

an $\alpha_D$ value stabilized after a few hours in solution ranging from $+120°$ and $+140°$;

a retention time of 8.2 min. in HPLC on C18 Bondapack column 300 mm×4 (15,000 plates/m) at a flow-rate of 1 ml/min. of water an as eluent;

a $C^{13}$ NMR spectrum showing signals at 99.6, 76.8, 73.4, 71.5, 71.1, and 60.5 ppm;

a $H^1$-NMR spectrum;

an IR spectrum having broad bands in the region 3600–3000 and 1200–1000 $cm^{-1}$;

an elementary composition of about C=45%; H=6%; O=48%; Na from 0 to 2%;

which consists of adding to said juice or to said bromelain trichloracetic acid, separating the precipitate by filtration and the clear liquid is then brought to a pH between 4.0 and 4.5 with sodium hydroxide, then ethyl alcohol in a volume ratio of respectively 0.3–0.6:1 is added, the precipitate separated, then ethyl alcohol is added to the filtrate in a ratio of respectively 1–2:1, a precipitate is obtained and said product is recovered from the precipitate.

4. The process according to claim 2 which is carried out in the presence of an antioxidant.

5. The process according to claim 3 which is carried out in the presence of an antioxidant.

6. A pharmaceutical composition having antiinflammatory and platelet antiaggregant activity which contains as the active principle a therapeutically effective amount of the product of claim 1 and at least one inert carrier.

7. A pharmaceutical composition according to claim 6 which contains 5 to 5000 picograms of the product of claim 1 per unit dose.

8. A pharmaceutical composition according to claim 6 suitable for the oral, parenteral, topical, rectal or inhalatory routes in the form of drops, solutions, syrups, capsules, tablets, vials, suppositories, creams, ointments or aerosols.

* * * * *